(12) United States Patent
Koizumi et al.

(10) Patent No.: US 7,579,175 B2
(45) Date of Patent: *Aug. 25, 2009

(54) PROCESS FOR PRODUCING N-ACETYLNEURAMINIC ACID

(75) Inventors: Satoshi Koizumi, Machida (JP); Kazuhiko Tabata, Hofu (JP); Tetsuo Endo, Machida (JP); Akio Ozaki, Hofu (JP)

(73) Assignee: Kyowa Hakko Bio Co., Ltd., Tokyo (JP)

( * ) Notice: Subject to any disclaimer, the term of this patent is extended or adjusted under 35 U.S.C. 154(b) by 365 days.

This patent is subject to a terminal disclaimer.

(21) Appl. No.: 10/338,872

(22) Filed: Jan. 9, 2003

(65) Prior Publication Data

US 2003/0109007 A1 Jun. 12, 2003

Related U.S. Application Data

(62) Division of application No. 09/645,321, filed on Aug. 25, 2000, now Pat. No. 6,846,656.

(30) Foreign Application Priority Data

Aug. 30, 1999 (JP) .................................. 11-242670

(51) Int. Cl.
C12P 7/58 (2006.01)
C12P 1/00 (2006.01)
C12Q 1/00 (2006.01)
C12N 9/24 (2006.01)
C12N 1/20 (2006.01)
C02F 3/34 (2006.01)
C07K 14/00 (2006.01)
C07H 21/04 (2006.01)

(52) U.S. Cl. ............................... 435/137; 435/4; 435/6; 435/41; 435/69.1; 435/183; 435/193; 435/200; 435/252.3; 435/262; 435/320.1; 530/350; 536/23.2; 536/23.4; 536/23.5; 536/23.7

(58) Field of Classification Search .................. 435/4, 435/6, 69.1, 183 T, 193, 200 T, 252–3 T, 435/320.1, 41 T, 262 T, 41, 183, 252.3, 262; 536/23.2, 23.4, 23.5, 23.7; 530/350
See application file for complete search history.

(56) References Cited

U.S. PATENT DOCUMENTS 5,071,750 A 12/1991 Kragl et al. .................. 435/94
5,665,574 A 9/1997 Tsukada et al. ............. 435/105

FOREIGN PATENT DOCUMENTS

JP 6-197778 7/1994
JP 10-4961 1/1998
WO 94/29476 12/1994

OTHER PUBLICATIONS

Vann(a) et al. (Glycobiology, 1997, vol. 7(5):697-701).*
Vann(b) et al. (J. Biol. Chem., 1987, vol. 262(36):17556-62).*
Maru et al. (Carbohydrate Research, 1998, vol. 306:575-578).*
Zhu, et al., "The effect of pfl gene knockout on the metabolism for optically pure . . . ", App. Microbiol. Biotech., vol. 64 (2004), pp. 367-375.
Martin, et al., "A facile procedure for the isolation of . . . ", Carbohydrate Research, vol. 56 (1977), pp. 423-425.
Uchida, et al., "Distribution of Neuraminidase in Arthrobacter . . . ", J. Biochem., vol. 82 (1977), pp. 1425-1433.
Kim, et al., "Enzymes in Carbohydrates Synthesis: N-Acetylneuraminic . . . ", J. Am. Chem. Soc., vol. 110 (1988), pp. 6481-6486.
Simon, et al., "Synthesis of CMP-NeuAc from N-Acetylglucosamine . . . ", J. Am. Chem. Soc., vol. 110 (1988), pp. 7159-7163.
Kragl, et al., "Enzymatic Two-step Synthesis of N-Acetylneuraminic", Agnew. Chem. Int. Ed. Engl., vol. 30, No. 7 (1991), pp. 827-828.
Maru, et al., "Simple and large-scale production of N-acetylneuraminic acid . . . ", Carbohydrate Research, vol. 306 (1998), pp. 575-578.
Vann, et al., "Purification and characterization of the . . . ", Glycobiology, vol. 7, No. 5 (1997), pp. 697-701.
Ohta, et al., "Complete nucleotide sequence of the E. coli-acetylneuraminate lyase", Nucleic Acids Research, vol. 13, No. 24 (1985), pp. 8843-8852.
Annunziato, et al., "Nucleotide Sequence and Genetic Analysis . . . " Journal of Bacteriology, vol. 177, No. 2 (1995), pp. 312-319.
Littlechild, et al., "A New Method for the Purification of 30S . . . ", Biochemistry, vol. 17, No. 16 (1978), pp. 3363-3369.
Maru, et al., "Molecular Cloning and Identification of . . . ", The Journal of Biological Chemistry, vol. 271, No. 27 (1996), pp. 16294-16299.
Yokoto, et al., "Pyruvic Acid Production by an F1—ATPase-defective Mutant . . . ", Biosci. Biotech. Biochem., vol. 58, No. 12 (1994), pp. 2164-2167.

(Continued)

Primary Examiner—Christian L Fronda
(74) Attorney, Agent, or Firm—Fitzpatrick, Cella, Harper & Scinto (57) ABSTRACT

The present invention provides a process for economically producing N-acetylneuraminic acid without using expensive materials such as pyruvic acid and phosphoenolpyruvic acid. The process comprises: allowing (i) a culture of a microorganism having N-acetylneuraminic acid aldolase activity or N-acetylneuraminic acid synthetase activity, or a treated matter of the culture, (ii) a culture of a microorganism capable of producing pyruvic acid or a treated matter of the culture, or a culture of a microorganism capable of producing phosphoenolpyruvic acid or a treated matter of the culture, (iii) N-acetylmannosamine, and (iv) an energy source which is necessary for the formation of pyruvic acid or phosphoenolpyruvic acid to be present in an aqueous medium to form and accumulate N-acetylneuraminic acid in the aqueous medium; and recovering N-acetylneuraminic acid from the aqueous medium.

10 Claims, 3 Drawing Sheets

OTHER PUBLICATIONS

Mahmoudian, et al., An efficient process for production of . . . , Enzyme and Microbial Technology, vol. 20 (1997), pp. 393-400.

Stäsche, et al., "A Bifunctional Enzym Catalyzes . . .", J. Biol. Chem., vol. 272, No. 39 (1997), pp. 24313-24318.

Stäsche, et al., J. Biol. Chem., vol. 272, No. 39 (1997), pp. 24319-24324.

Vann, et al., "Purification Properties, and Genetic Location of . . .", J. Biol. Chem., vol. 262, No. 36 (1987), pp. 17556-17562.

Vann, et al., "Purification and Characterization of the . . ." Glycobiology, vol. 7, No. 5 (1997), pp. 697-701.

Warren, et al., "The Biosynthesis of N-Acetylneuraminic Acid", Biochem. Biophys. Research Communs, vol. 4, No. 3 (1961), pp. 232-235.

Kragl, et al., "N-Acetylneuraminic Acid From a Rare Chemical from Natural Sources . . . ", Ann. N.Y. Acad. Sci (1995), pp. 300-305.

Vann, et al., "Purification and Characterization of the *Escherichia coli* K1 *neuB* gene product . . . ", Glycobiology (1997), vol. 7, No. 5, pp. 697-701.

Chemical Abstract, Database Accession No. XP-00218097, Kragl, "Reaction technology for Continuous enzymic . . . ", (1992).

* cited by examiner

SEQUENCE LISTING

```
<160> NUMBER OF SEQ ID NOS: 8

<210> SEQ ID NO 1
<211> LENGTH: 391
<212> TYPE: PRT
<213> ORGANISM: Synechocystis sp.(PCC6803)

<400> SEQUENCE: 1

Met Ile Ala His Arg Arg Gln Glu Leu Ala Gln Gln Tyr Tyr Gln Ala
 1               5                  10                  15

Leu His Gln Asp Val Leu Pro Phe Trp Glu Lys Tyr Ser Leu Asp Arg
             20                  25                  30

Gln Gly Gly Gly Tyr Phe Thr Cys Leu Asp Arg Lys Gly Gln Val Phe
         35                  40                  45

Asp Thr Asp Lys Phe Ile Trp Leu Gln Asn Arg Gln Val Trp Gln Phe
     50                  55                  60

Ala Val Phe Tyr Asn Arg Leu Glu Pro Lys Pro Gln Trp Leu Glu Ile
 65                  70                  75                  80

Ala Arg His Gly Ala Asp Phe Leu Ala Arg His Gly Arg Asp Gln Asp
                 85                  90                  95

Gly Asn Trp Tyr Phe Ala Leu Asp Gln Glu Gly Lys Pro Leu Arg Gln
            100                 105                 110

Pro Tyr Asn Val Phe Ser Asp Cys Phe Ala Ala Met Ala Phe Ser Gln
        115                 120                 125

Tyr Ala Leu Ala Ser Gly Ala Gln Glu Ala Lys Ala Ile Ala Leu Gln
    130                 135                 140
```

```
Ala Tyr Asn Asn Val Leu Arg Arg Gln His Asn Pro Lys Gly Gln Tyr
145                 150                 155                 160

Glu Lys Ser Tyr Pro Gly Thr Arg Pro Leu Lys Ser Leu Ala Val Pro
                165                 170                 175

Met Ile Leu Ala Asn Leu Thr Leu Glu Met Glu Trp Leu Leu Pro Pro
            180                 185                 190

Thr Thr Val Glu Glu Val Leu Ala Gln Thr Val Arg Glu Val Met Thr
        195                 200                 205

Asp Phe Leu Asp Pro Glu Ile Gly Leu Met Arg Glu Ala Val Thr Pro
    210                 215                 220

Thr Gly Glu Phe Val Asp Ser Phe Glu Gly Arg Leu Leu Asn Pro Gly
225                 230                 235                 240

His Gly Ile Glu Ala Met Trp Phe Met Met Asp Ile Ala Gln Arg Ser
                245                 250                 255

Gly Asp Arg Gln Leu Gln Glu Gln Ala Ile Ala Val Val Leu Asn Thr
                260                 265                 270

Leu Glu Tyr Ala Trp Asp Glu Glu Phe Gly Gly Ile Phe Tyr Phe Leu
            275                 280                 285

Asp Arg Gln Gly His Pro Pro Gln Leu Glu Trp Asp Gln Lys Leu
        290                 295                 300

Trp Trp Val His Leu Glu Thr Leu Val Ala Leu Ala Lys Gly His Gln
305                 310                 315                 320

Ala Thr Gly Gln Glu Lys Cys Trp Gln Trp Phe Glu Arg Val His Asp
                325                 330                 335

Tyr Ala Trp Ser His Phe Ala Asp Pro Glu Tyr Gly Glu Trp Phe Gly
                340                 345                 350

Tyr Leu Asn Arg Arg Gly Glu Val Leu Leu Asn Leu Lys Gly Gly Lys
            355                 360                 365

Trp Lys Gly Cys Phe His Val Pro Arg Ala Leu Trp Leu Cys Ala Glu
370                 375                 380

Thr Leu Gln Leu Pro Val Ser
385                 390

<210> SEQ ID NO 2
<211> LENGTH: 1173
<212> TYPE: DNA
<213> ORGANISM: Synechocystis sp.(PCC6803)

<400> SEQUENCE: 2 atg att gcc cat cgc cgt cag gag tta gcc cag caa tat tac cag gct      48
Met Ile Ala His Arg Arg Gln Glu Leu Ala Gln Gln Tyr Tyr Gln Ala
  1               5                  10                  15 tta cac cag gac gta ttg ccc ttt tgg gaa aaa tat tcc ctc gat cgc      96
Leu His Gln Asp Val Leu Pro Phe Trp Glu Lys Tyr Ser Leu Asp Arg
             20                  25                  30 cag ggg ggc ggt tac ttt acc tgc tta gac cgt aaa ggc cag gtt ttt     144
Gln Gly Gly Gly Tyr Phe Thr Cys Leu Asp Arg Lys Gly Gln Val Phe
         35                  40                  45 gac aca gat aaa ttc att tgg tta caa aac cgt cag gta tgg cag ttt     192
Asp Thr Asp Lys Phe Ile Trp Leu Gln Asn Arg Gln Val Trp Gln Phe
     50                  55                  60 gcc gtt ttc tac aac cgt ttg gaa cca aaa ccc caa tgg tta gaa att     240
Ala Val Phe Tyr Asn Arg Leu Glu Pro Lys Pro Gln Trp Leu Glu Ile
 65                  70                  75                  80 gcc cgc cat ggt gct gat ttt tta gct cgc cac ggc cga gat caa gac     288
Ala Arg His Gly Ala Asp Phe Leu Ala Arg His Gly Arg Asp Gln Asp
```

```
                      85                    90                    95
ggt aat tgg tat ttt gct ttg gat cag gaa ggc aaa ccc ctg cgt caa        336
Gly Asn Trp Tyr Phe Ala Leu Asp Gln Glu Gly Lys Pro Leu Arg Gln
            100                 105                 110 ccc tat aac gtt ttt tcc gat tgc ttc gcc gcc atg gcc ttt agt caa        384
Pro Tyr Asn Val Phe Ser Asp Cys Phe Ala Ala Met Ala Phe Ser Gln
            115                 120                 125 tat gcc tta gcc agt ggg gcg cag gaa gct aaa gcc att gcc ctg cag        432
Tyr Ala Leu Ala Ser Gly Ala Gln Glu Ala Lys Ala Ile Ala Leu Gln
            130                 135                 140 gcc tac aat aac gtc cta cgc cgt cag cac aat ccc aaa ggt caa tac        480
Ala Tyr Asn Asn Val Leu Arg Arg Gln His Asn Pro Lys Gly Gln Tyr
145                 150                 155                 160 gag aag tcc tat cca ggt act aga ccc ctc aaa tcc ctg gcg gtg ccg        528
Glu Lys Ser Tyr Pro Gly Thr Arg Pro Leu Lys Ser Leu Ala Val Pro
                    165                 170                 175 atg att tta gcc aac ctc acc ctg gag atg gaa tgg tta tta ccg cct        576
Met Ile Leu Ala Asn Leu Thr Leu Glu Met Glu Trp Leu Leu Pro Pro
                180                 185                 190 act acc gtg gaa gag gtg ttg gcc caa acc gtc aga gaa gtg atg acg        624
Thr Thr Val Glu Glu Val Leu Ala Gln Thr Val Arg Glu Val Met Thr
            195                 200                 205 gat ttc ctc gac cca gaa ata gga tta atg cgg gaa gcg gtg acc ccc        672
Asp Phe Leu Asp Pro Glu Ile Gly Leu Met Arg Glu Ala Val Thr Pro
210                 215                 220 aca gga gaa ttt gtt gat agt ttt gaa ggg cgg ttg ctc aac cca gga        720
Thr Gly Glu Phe Val Asp Ser Phe Glu Gly Arg Leu Leu Asn Pro Gly
225                 230                 235                 240 cac ggc att gaa gcc atg tgg ttc atg atg gac att gcc caa cgc tcc        768
His Gly Ile Glu Ala Met Trp Phe Met Met Asp Ile Ala Gln Arg Ser
                245                 250                 255 ggc gat cgc cag tta cag gag caa gcc att gca gtg gtg ttg aac acc        816
Gly Asp Arg Gln Leu Gln Glu Gln Ala Ile Ala Val Val Leu Asn Thr
            260                 265                 270 ctg gaa tat gcc tgg gat gaa gaa ttt ggt ggc ata ttt tat ttc ctt        864
Leu Glu Tyr Ala Trp Asp Glu Glu Phe Gly Gly Ile Phe Tyr Phe Leu
            275                 280                 285 gat cgc cag ggc cac cct ccc caa caa ctg gaa tgg gac caa aag ctc        912
Asp Arg Gln Gly His Pro Pro Gln Gln Leu Glu Trp Asp Gln Lys Leu
            290                 295                 300 tgg tgg gta cat ttg gaa acc ctg gtt gcc cta gcc aag ggc cac caa        960
Trp Trp Val His Leu Glu Thr Leu Val Ala Leu Ala Lys Gly His Gln
305                 310                 315                 320 gcc act ggc caa gaa aaa tgt tgg caa tgg ttt gag cgg gtc cat gat       1008
Ala Thr Gly Gln Glu Lys Cys Trp Gln Trp Phe Glu Arg Val His Asp
                325                 330                 335 tac gcc tgg agt cat ttc gcc gat cct gag tat ggg gaa tgg ttt ggc       1056
Tyr Ala Trp Ser His Phe Ala Asp Pro Glu Tyr Gly Glu Trp Phe Gly
            340                 345                 350 tac ctg aat cgc cgg gga gag gtg tta ctc aac cta aaa ggg ggg aaa       1104
Tyr Leu Asn Arg Arg Gly Glu Val Leu Leu Asn Leu Lys Gly Gly Lys
            355                 360                 365 tgg aaa ggg tgc ttc cac gtg ccc cga gct ctg tgg ctc tgt gcg gaa       1152
Trp Lys Gly Cys Phe His Val Pro Arg Ala Leu Trp Leu Cys Ala Glu
370                 375                 380 act ctc caa ctt ccg gtt agt                                           1173
Thr Leu Gln Leu Pro Val Ser
385                 390
```

```
<210> SEQ ID NO 3
<211> LENGTH: 24
<212> TYPE: DNA
<213> ORGANISM: Artificial Sequence
<220> FEATURE:
<223> OTHER INFORMATION: Synthetic DNA

<400> SEQUENCE: 3
gtgtaagctt tctgtatggg gtgt                                              24

<210> SEQ ID NO 4
<211> LENGTH: 26
<212> TYPE: DNA
<213> ORGANISM: Artificial Sequence
<220> FEATURE:
<223> OTHER INFORMATION: Synthetic DNA

<400> SEQUENCE: 4 gcaggatcc caaccaggca gcggaa                                             26

<210> SEQ ID NO 5
<211> LENGTH: 32
<212> TYPE: DNA
<213> ORGANISM: Artificial Sequence
<220> FEATURE:
<223> OTHER INFORMATION: Synthetic DNA

<400> SEQUENCE: 5
tttatcgata ttaattaggg ggaatgaatg ag                                     32

<210> SEQ ID NO 6
<211> LENGTH: 33
<212> TYPE: DNA
<213> ORGANISM: Artificial Sequence
<220> FEATURE:
<223> OTHER INFORMATION: Synthetic DNA

<400> SEQUENCE: 6
tttggatcct cattattccc cctgattttt gaa                                    33

<210> SEQ ID NO 7
<211> LENGTH: 36
<212> TYPE: DNA
<213> ORGANISM: Artificial Sequence
<220> FEATURE:
<223> OTHER INFORMATION: Synthetic DNA

<400> SEQUENCE: 7
taaatcgata tttgtatgat tgcccatcgc cgtcag                                 36

<210> SEQ ID NO 8
<211> LENGTH: 36
<212> TYPE: DNA
<213> ORGANISM: Artificial Sequence
<220> FEATURE:
<223> OTHER INFORMATION: Synthetic DNA

<400> SEQUENCE: 8
aaaggatcct taactaaccg gaagttggag agtttc                                 36
```

PROCESS FOR PRODUCING N-ACETYLNEURAMINIC ACID

This application is a division of application Ser. No. 09/645,321 filed Aug. 25, 2000, issued as U.S. Pat. No. 6,846,656.

BACKGROUND OF THE INVENTION

The present invention relates to a process for producing N-acetylneuraminic acid by using a microorganism having N-acetylneuraminic acid aldolase activity or N-acetylneuraminic acid synthetase activity.

It is known that N-acetylneuraminic acid can be produced by extraction, decomposition or by use of enzymes.

An example of a known method by extraction is extraction from a nest of sea swallows, etc. [Carbohydrate Research, 56, 423 (1977)].

An example of a known method by decomposition is decomposition of colominic acid, which is an N-acetylneuraminic acid polymer produced by *Escherichia coli*, etc. [J. Biochem., 82, 1425 (1977)].

Known methods utilizing enzymes include the following: methods using N-acetylneuraminic acid aldolase, pyruvic acid and N-acetylmannosamine [J. Am. Chem. Soc., 110, 6481 (1988); J. Am. Chem. Soc., 110, 7159 (1988)]; a method using N-acetylneuraminic acid aldolase, pyruvic acid and N-acetylglucosamine under alkaline conditions (U.S. Pat. No. 5,665,574); methods using N-acetylneuraminic acid aldolase, N-acetylglucosamine 2-epimerase, pyruvic acid and N-acetylglucosamine [Angew. Chem. Int. Ed. Eng., 30, 827 (1991); Carbohydrate Research, 306, 575 (1998)]; and methods using N-acetylneuraminic acid synthetase, phosphoenolpyruvic acid and N-acetylmannosamine [Japanese Published Unexamined Patent Application No. 4961/98; Glycobiology, 7, 697 (1997)].

The above methods for producing N-acetylneuraminic acid require complicated operations or expensive materials such as pyruvic acid and phosphoenolpyruvic acid, and an economical method for producing N-acetylneuraminic acid has not been established yet.

So far, there has been no report describing or suggesting that N-acetylneuraminic acid can be produced by utilizing a culture of a microorganism or a treated matter thereof.

As for the N-acetylneuraminic acid aldolase, those derived from animals and plants are known, and it is known that microorganisms belonging to the genus *Escherichia* have the activity of this enzyme. Also known is the presence of the gene encoding this enzyme, nanA, in an *Escherichia coli* strain [Nucleic Acids Res., 13, 8843 (1985)].

N-Acetylneuraminic acid synthetase is known to be present in microorganisms belonging to the genera *Escherichia*, *Neisseria* and *Streptococcus*, etc., and it is known that an *Escherichia coli* strain has the gene encoding this enzyme, neuB [J. Bacteriol., 177, 312 (1995)].

N-Acetylglucosamine 2-epimerase is known to be present in pigs and rats. The properties of the enzyme derived from pig have been investigated [Biochemistry, 17, 3363 (1970)] and the gene encoding the enzyme [J. Biol. Chem., 271, 16294 (1996)] has been obtained. So far, no microorganism having the activity of this enzyme is known.

As to the production of pyruvic acid, a process for producing pyruvic acid by using a mutant of *Escherichia coli* is known [Biosci. Biotech. Biochem., 58, 2164 (1994)].

As to the production of phosphoenolpyruvic acid, a process for producing phosphoenolpyruvic acid by using microorganisms of *Saccharomyces*, etc. is known (Japanese Published Unexamined Patent Application No. 197778/94).

An object of the present invention is to provide a process for economically producing N-acetylneuraminic acid without using expensive materials such as pyruvic acid and phosphoenolpyruvic acid. A further object of the present invention is to provide a process for producing N-acetylneuraminic acid without using expensive N-acetylmannosamine.

SUMMARY OF THE INVENTION

The present inventors have made an intensive investigation to attain the above objects and have found that N-acetylneuraminic acid can be efficiently produced from inexpensive materials by utilizing a microorganism which is capable of producing pyruvic acid or phosphoenolpyruvic acid. The present invention has been completed based on this finding.

The present invention relates to the following (1)-(11).

(1) A process for producing N-acetylneuraminic acid which comprises:

allowing (i) a culture of a microorganism having N-acetylneuraminic acid aldolase activity or N-acetylneuraminic acid synthetase activity, or a treated matter of the culture, (ii) a culture of a microorganism capable of producing pyruvic acid or a treated matter of the culture when a microorganism having N-acetylneuraminic acid aldolase activity is used in (i) above, or a culture of a microorganism capable of producing phosphoenolpyruvic acid or a treated matter of the culture when a microorganism having N-acetylneuraminic acid synthetase activity is used in (i) above, (iii) N-acetylmannosamine, and (iv) an energy source which is necessary for the formation of pyruvic acid or phosphoenolpyruvic acid to be present in an aqueous medium to form and accumulate N-acetylneuraminic acid in the aqueous medium; and recovering N-acetylneuraminic acid from the aqueous medium.

(2) The process according to the above (1) wherein said N-acetylmannosamine is produced by allowing a culture of a microorganism having N-acetylglucosamine 2-epimerase activity or a treated matter of the culture and N-acetylglucosamine to be present in an aqueous medium to form and accumulate N-acetylmannosamine in the aqueous medium.

(3) The process according to the above (2) wherein said microorganism having N-acetylglucosamine 2-epimerase activity carries a recombinant DNA composed of a DNA fragment comprising DNA encoding N-acetylglucosamine 2-epimerase and a vector.

(4) The process according to the above (3) wherein said DNA encoding N-acetylglucosamine 2-epimerase is DNA derived from a microorganism belonging to the genus *Synechocystis*.

(5) The process according to the above (3) or (4) wherein said DNA encoding N-acetylglucosamine 2-epimerase is selected from the group consisting of:

(a) DNA encoding a protein having the amino acid sequence shown in SEQ ID NO: 1; and (b) DNA having the nucleotide sequence shown in SEQ ID NO: 2.

(6) The process according to any of the above (1)-(5) wherein said microorganism having N-acetylneuraminic acid aldolase activity is a microorganism belonging to the genus *Escherichia* or *Corynebacterium*.

(7) The process according to any of the above (1)-(6) wherein said microorganism having N-acetylneuraminic acid synthetase activity is a microorganism belonging to a genus selected from the group consisting of *Escherichia, Neisseria* and *Streptococcus*.

(8) The process according to any of the above (1)-(7) wherein said microorganism capable of producing pyruvic acid is a microorganism belonging to a genus selected from the group consisting of *Escherichia, Corynebacterium* and *Saccharomyces*.

(9) The process according to any of the above (1)-(8) wherein said microorganism capable of producing phosphoenolpyruvic acid is a microorganism belonging to a genus selected from the group consisting of *Escherichia, Corynebacterium* and *Saccharomyces*.

(10) The process according to any of the above (6)-(9) wherein said microorganism belonging to the genus *Escherichia* is *Escherichia coli*.

(11) The process according to the above (6), (8) or (9) wherein said microorganism belonging to the genus *Corynebacterium* is *Corynebacterium ammoniagenes, Corynebacterium glutamicum* or *Corynebacterium acetoacidophilum*.

EXPLANATION OF SYMBOLS

Amp$^r$: Ampicillin resistance gene

P$_L$: P$_L$ promoter cI857: cI857 repressor

P$_{lac}$: lac promoter slr1975: N-Acetylglucosamine 2-epimerase gene nanA: N-Acetylneuraminic acid aldolase gene neuB: N-Acetylneuraminic acid synthetase gene

DETAILED DESCRIPTION OF THE INVENTION

In the process of the present invention, any microorganism having N-acetylneuraminic acid aldolase activity can be used. For example, microorganisms belonging to the genus *Escherichia* or *Corynebacterium* may be used.

Examples of the microorganisms belonging to the genus *Escherichia* are those of the species *Escherichia coli*. Examples of the microorganisms belonging to the genus *Corynebacterium* are those of the species *Corynebacterium ammoniagenes, Corynebacterium glutamicum* and *Corynebacterium acetoacidophilum*.

Also useful are transformants with N-acetylneuraminic acid aldolase activity enhanced by recombinant DNA techniques. Examples of such transformants include microorganisms carrying a recombinant DNA comprising nanA gene derived from *Escherichia coli* [Nucleic Acids Res., 13, 8843 (1985)], specifically, *Escherichia coli* NM522/pTA3.

Any microorganism having N-acetylneuraminic acid synthetase activity can be used in the process of the present invention. For example, microorganisms belonging to the genus *Escherichia, Neisseria* or *Streptococcus* may be used.

Examples of the microorganisms belonging to the genus *Escherichia* are those of the species *Escherichia coli*.

Also useful are transformants with N-acetylneuraminic acid synthetase activity enhanced by recombinant DNA techniques. Examples of such transformants include microorganisms carrying a recombinant DNA comprising neuB gene derived from *Escherichia coli* [J. Bacteriol., 177, 312 (1995)], specifically, *Escherichia coli* NM522/pYP18.

Any microorganism capable of producing pyruvic acid can be used in the process of the present invention. Examples of suitable microorganisms are those of the species *Escherichia coli, Corynebacterium ammoniagenes, Corynebacterium glutamicum, Corynebacterium acetoacidophilum* and *Saccharomyces cerevisiae*. Also useful are microorganisms with pyruvic acid productivity enhanced by mutagenesis or recombinant DNA techniques. For example, the *Escherichia coli* mutant described in Biosci. Biotech. Biochem., 58, 2164 (1994) can be used.

Any microorganism capable of producing phosphoenolpyruvic acid can be used in the process of the present invention. Examples of suitable microorganisms are those of the species *Escherichia coli, Corynebacterium ammoniagenes, Corynebacterium glutamicum, Corynebacterium acetoacidophilum* and *Saccharomyces cerevisiae*. An example of the microorganism of the species *Saccharomyces cerevisiae* is the strain described in Japanese Published Unexamined Patent Application No. 197778/94. Also useful are microorganisms with phosphoenolpyruvic acid productivity enhanced by mutagenesis or recombinant DNA techniques.

Any microorganism having N-acetylglucosamine 2-epimerase activity can be used in the process of the present invention. Suitable microorganisms include transformants with N-acetylglucosamine 2-epimerase activity enhanced by recombinant DNA techniques. Specific examples of such transformants are *Escherichia coli* carrying the recombinant DNA pEPI1 comprising the N-acetylglucosamine 2-epimerase gene derived from pig (FERM BP-4602: U.S. Pat. No. 5,795,767) and; *Escherichia coli* NM522/pYP16 carrying a recombinant DNA comprising the N-acetylglucosamine 2-epimerase gene derived from a microorganism belonging to the genus *Synechocystis*.

An example of the N-acetylglucosamine 2-epimerase gene derived from a microorganism belonging to the genus *Synechocystis* is the gene encoding a polypeptide having the amino acid sequence shown in SEQ ID NO: 1 which exists on the chromosome of *Synechocystis* sp. PCC6803, more specifically, the gene having the nucleotide sequence shown in SEQ ID NO: 2 (slr1975). The polypeptide having the amino acid sequence shown in SEQ ID NO: 1 and the DNA having the nucleotide sequence shown in SEQ ID NO: 2 have been obtained for the first time by the present inventors according to the procedure described later in an example.

A microorganism having N-acetylneuraminic acid aldolase activity and the ability to produce pyruvic acid can be used alone for the production of N-acetylneuraminic acid from N-acetylmannosamine. In cases where the microorganism employed is weak or lacking in any of the above properties, it may be used in combination with a microorganism which can complement such property for producing N-acetylneuraminic acid.

N-Acetylmannosamine useful in the production of N-acetylneuraminic acid includes N-acetylmannosamine preparations (e.g., commercial products) and N-acetylmannosamine prepared from N-acetylglucosamine by chemical reaction under alkaline conditions or by enzymatic conversion using N-acetylglucosamine 2-epimerase. Also useful are preparations containing N-acetylmannosamine formed and accumulated by allowing a culture of a microorganism having N-acetylglucosamine 2-epimerase activity or a treated matter of the culture and N-acetylglucosamine to be present in an aqueous medium, and N-acetylmannosamine purified from such preparations.

A microorganism having N-acetylneuraminic acid aldolase activity, N-acetylglucosamine 2-epimerase activity and the ability to produce pyruvic acid can be used alone for the production of N-acetylneuraminic acid from N-acetylglucosamine. In cases where the microorganism employed is weak or lacking in any of the above properties, it may be used in combination with a microorganism which can complement such property for producing N-acetylneuraminic acid.

N-Acetylglucosamine useful in the production of N-acetylneuraminic acid includes N-acetylglucosamine preparations (e.g., commercial products).

A microorganism having N-acetylneuraminic acid synthetase activity and the ability to produce phosphoenolpyruvic acid can also be used alone for the production of N-acetylneuraminic acid from N-acetylmannosamine. In cases where the microorganism employed is weak or lacking in any of the above properties, it may be used in combination with a microorganism which can complement such property for producing N-acetylneuraminic acid.

Further, a microorganism having N-acetylneuraminic acid synthetase activity, N-acetylglucosamine 2-epimerase activity and the ability to produce phosphoenolpyruvic acid can be used alone for the production of N-acetylneuraminic acid from N-acetylglucosamine. In cases where the microorganism employed is weak or lacking in any of the above properties, it may be used in combination with a microorganism which can complement such property for producing N-acetylneuraminic acid.

The microorganisms employed in the production of N-acetylneuraminic acid or N-acetylmannosamine may be subjected to reaction to form the product during their growth stage. Alternatively, after the completion of culturing of a microorganism, the resulting culture or a treated matter of the culture may be subjected to reaction.

As described above, microorganisms prepared by using recombinant DNA techniques can be used in the production of N-acetylneuraminic acid or N-acetylmannosamine. Gene manipulating operations such as isolation and purification of plasmid DNA comprising a desired gene from a microorganism carrying the plasmid, cleavage of plasmid DNA with restriction enzymes, isolation and purification of cleaved DNA fragments, enzymatic ligation of DNA fragments, and transformation with recombinant DNA can be carried out according to known methods [e.g., Molecular Cloning, A Laboratory Manual, Second Edition, Cold Spring Harbor Laboratory Press (1989) (hereinafter referred to as Molecular Cloning, Second Edition); Current Protocols in Molecular Biology, John Wiley & Sons (1987-1997) (hereinafter referred to as Current Protocols in Molecular Biology)]. Polymerase chain reaction (hereinafter referred to as PCR) can be carried out by a known method [PCR Protocols, Academic Press (1990)].

A gene concerned in the production of N-acetylneuraminic acid or N-acetylmannosamine can be expressed in a host by preparing a DNA fragment of an appropriate length containing the gene from a DNA fragment containing the gene by use of restriction enzymes or PCR, inserting the prepared DNA fragment into an appropriate expression vector at a site downstream of the promoter, and then introducing the expression vector comprising the above DNA into a host cell suited for the expression vector.

As the host cell, any bacterial cells, yeast cells, etc. which are capable of expressing a desired gene can be used.

The expression vectors that can be employed are those capable of autonomous replication or integration into chromosome in the above host cells and comprising a promoter at a position appropriate for the transcription of a desired DNA.

When a procaryotic cell such as a bacterial cell is used as the host cell, it is preferred that the expression vector for a gene is a recombinant DNA which is capable of autonomous replication in the procaryotic cell and which comprises a promoter, a ribosome binding sequence, the desired DNA, and a transcription termination sequence. The vector may further comprise a gene regulating the promoter.

Examples of suitable expression vectors are pBTrp2 (Roche Diagnostics), pBTac1 (Roche Diagnostics), pBTac2 (Roche Diagnostics), pHelix1 (Roche Diagnostics), pKK233-2 (Amersham Pharmacia Biotech), pKK223-3 (Amersham Pharmacia Biotech), pGEX-2T (Amersham Pharmacia Biotech), pSE280 (Invitrogen), pGEMEX-1 (Promega), pQE-8 (QIAGEN), pQE-30 (QIAGEN), pET-3 (Novagen), pKYP10 (Japanese Published Unexamined Patent Application No. 110600/83), pKYP200 [Agric. Biol. Chem., 48, 669 (1984)], pLSA1 [Agric. Biol. Chem., 53, 277(1989)], pGEL1 [Proc. Natl. Acad. Sci. USA, 82, 4306 (1985)], pBluescript II SK+ (Stratagene), pBluescript II SK− (Stratagene), pTrS30 [prepared from *Escherichia coli* JM109/pTrS30 (FERM BP-5407)], pTrS32 [prepared from *Escherichia coli* JM109/pTrS32 (FERM BP-5408)], pUC19 [Gene, 33, 103 (1985)], pSTV28 (Takara Shuzo Co., Ltd.), pUC118 (Takara Shuzo Co., Ltd.), pPAC31 (WO 98/12343) and pPA1 (Japanese Published Unexamined Patent Application No. 233798/88).

As the promoter, any promoters capable of functioning in host cells such as *Escherichia coli* can be used. For example, promoters derived from *Escherichia coli* or phage, such as trp promoter (Ptrp), lac promoter (Plac), $P_L$ promoter, $P_R$ promoter and $P_{SE}$ promoter, SPO1 promoter, SPO2 promoter and penP promoter can be used. Artificially modified promoters such as a promoter in which two Ptrp are combined in tandem, tac promoter, lacT7 promoter and letI promoter, etc. can also be used.

It is preferred to use a plasmid in which the distance between the Shine-Dalgarno sequence (ribosome binding sequence) and the initiation codon is adjusted to an appropriate length (e.g., 6-18 bases).

In the recombinant DNA of the present invention, the transcription termination sequence is not essential for the expression of the desired DNA, but it is preferred that the transcription termination sequence lie immediately downstream of the structural gene.

Examples of suitable procaryotes are microorganisms belonging to the genera *Escherichia*, *Serratia*, *Bacillus*, *Brevibacterium*, *Corynebacterium*, *Microbacterium* and *Pseudomonas*, specifically, *Escherichia coli* XL1-Blue, *Escherichia coli* XL2-Blue, *Escherichia coli* DH1, *Escherichia coli* MC1000, *Escherichia coli* W1485, *Escherichia coli* NM522, *Escherichia coli* JM109, *Escherichia coli* HB101, *Escherichia coli* No. 49, *Escherichia coli* W3110, *Escherichia coli* NY49, *Serratia ficaria*, *Serratia fonticola*, *Serratia liquefaciens*, *Serratia marcescens*, *Bacillus subtilis*, *Bacillus amyloliquefaciens*, *Brevibacterium immariophilum* ATCC 14068, *Brevibacterium saccharolyticum* ATCC 14066, *Corynebacterium ammoniagenes*, *Corynebacterium glutamicum* ATCC 13032, *Corynebacterium glutamicum*

ATCC 14067, *Corynebacterium glutamicum* ATCC 13869, *Corynebacterium acetoacidophilum* ATCC 13870, *Microbacterium ammoniaphilum* ATCC 15354 and *Pseudomonas* sp. D-0110.

Introduction of the recombinant DNA can be carried out by any of the methods for introducing DNA into the above host cells, for example, the method using calcium ion [Proc. Natl. Acad. Sci. USA, 69, 2110 (1972)], the protoplast method (Japanese Published Unexamined Patent Application No. 248394/88) and electroporation [Nucleic Acids Research, 16, 6127 (1988)].

When a yeast cell is used as the host cell, YEp13 (ATCC 37115), YEp24 (ATCC 37051), YCp50 (ATCC 37419), pHS19, pHS15, etc. can be used as the expression vector.

As the promoter, any promoters capable of functioning in yeast cells can be used. Suitable promoters include PHO5 promoter, PGK promoter, GAP promoter, ADH promoter, gal 1 promoter, gal-10 promoter, heat shock polypeptide promoter, MF α 1 promoter, CUP 1 promoter, etc.

Examples of suitable host cells are cells of yeast strains belonging to the genera *Saccharomyces, Schizosaccharomyces, Kluyveromyces, Trichosporon, Schwanniomyces, Pichia* and *Candida*, specifically, *Saccharomyces cerevisiae, Schizosaccharomyces pombe, Kluyveromyces lactis, Trichosporon pullulans, Schwanniomyces alluvius, Pichia pastoris* and *Candida utilis*.

Introduction of the recombinant DNA can be carried out by any of the methods for introducing DNA into yeast cells, for example, electroporation [Methods in Enzymol., 194, 182 (1990)], the spheroplast method [Proc. Natl. Acad. Sci. USA, 81, 4889 (1984)] and the lithium acetate method [J. Bacteriol., 153, 163 (1983)].

Culturing of the transformant of the present invention can be carried out by conventional methods for culturing the host cell of the transformant. For the culturing of the transformant prepared by using a procaryotic cell such as *Escherichia coli* cell or a eucaryotic cell such as a yeast cell as the host cell, any of natural media and synthetic media can be used insofar as it is a medium suitable for efficient culturing of the transformant which contains carbon sources, nitrogen sources, inorganic substances, etc. which can be assimilated by the host used.

As the carbon sources, any carbon sources which can be assimilated by the host can be used. Examples of suitable carbon sources include carbohydrates such as glucose, fructose, sucrose, molasses containing them, starch and starch hydrolyzate; organic acids such as acetic acid and propionic acid; and alcohols such as ethanol and propanol.

As the nitrogen sources, ammonia, ammonium salts of inorganic or organic acids such as ammonium chloride, ammonium sulfate, ammonium acetate and ammonium phosphate, and other nitrogen-containing compounds can be used as well as peptone, meat extract, yeast extract, corn steep liquor, casein hydrolyzate, soybean cake, soybean cake hydrolyzate, and various fermented cells and digested products thereof.

Examples of the inorganic substances include potassium dihydrogenphosphate, dipotassium hydrogenphosphate, magnesium phosphate, magnesium sulfate, sodium chloride, ferrous sulfate, manganese sulfate, copper sulfate and calcium carbonate.

Culturing is usually carried out under aerobic conditions, for example, by shaking culture or submerged spinner culture under aeration, at 15-40° C. for 5 hours to 7 days. The pH is maintained at 3.0-9.0 during the culturing. The pH adjustment is carried out by using an inorganic or organic acid, an alkali solution, urea, calcium carbonate, ammonia, etc.

If necessary, antibiotics such as ampicillin and tetracycline may be added to the medium during the culturing.

When a microorganism transformed with an expression vector comprising an inducible promoter is cultured, an inducer may be added to the medium, if necessary. For example, in the case of a microorganism transformed with an expression vector comprising lac promoter, isopropyl-β-D-thiogalactopyranoside or the like may be added to the medium; and in the case of a microorganism transformed with an expression vector comprising trp promoter, indoleacrylic acid or the like may be added.

The treated matters of a culture include concentrated culture, dried culture, cells obtained by centrifuging the culture, products obtained by treating the cells by various means such as drying, freeze-drying, treatment with a surfactant, ultrasonication, mechanical friction, treatment with a solvent, enzymatic treatment, protein fractionation and immobilization, an enzyme preparation obtained by extracting the cells, etc.

The amount of each microorganism used in the production of N-acetylneuraminic acid or N-acetylmannosamine is 1-500 g/l, preferably 1-300 g/l, as wet cells.

As the energy source which is necessary for the formation of pyruvic acid or phosphoenolpyruvic acid, any substance can be used that promotes the formation of pyruvic acid or phosphoenolpyruvic acid. Examples of preferred substances are glucose and fructose. The substances may be used usually at a concentration of 10-300 g/l.

Aqueous media useful in the production of N-acetylneuraminic acid or N-acetylmannosamine include water, buffers such as phosphate buffer, carbonate buffer, acetate buffer, borate buffer, citrate buffer and Tris buffer, alcohols such as methanol and ethanol, esters such as ethyl acetate, ketones such as acetone, amides such as acetamide, etc. Also useful is a medium or culture broth of a microorganism used in the process for producing N-acetylneuraminic acid or N-acetylmannosamine.

If necessary, a chelating agent (e.g., phytic acid), a surfactant or an organic solvent may be added in the process for producing N-acetylneuraminic acid or N-acetylmannosamine.

Any surfactant that promotes the formation of N-acetylneuraminic acid or N-acetylmannosamine can be used. Suitable surfactants include nonionic surfactants such as polyoxyethylene octadecylamine (e.g., Nymeen S-215, NOF Corporation), cationic surfactants such as cetyltrimethylammonium bromide and alkyldimethyl benzylammonium chloride (e.g., Cation F2-40E, NOF Corporation), anionic surfactants such as lauroyl sarcosinate, and tertiary amines such as alkyldimethylamine (e.g., Tertiary Amine FB, NOF Corporation), which may be used alone or in combination. The surfactant is usually used at a concentration of 0.1-50 g/l.

As the organic solvent, xylene, toluene, aliphatic alcohols, acetone, ethyl acetate, etc. may be used usually at a concentration of 0.1-50 ml/l.

The reaction for forming N-acetylneuraminic acid or N-acetylmannosamine is carried out in an aqueous medium at pH 5-10, preferably pH 6-8, at 20-50° C. for 1-96 hours.

Adenine, adenosine 5'-monotriphosphate (AMP), adenosine 5'-triphosphate (ATP), magnesium sulfate, magnesium chloride, etc. may be added for promoting the reaction. Adenine, AMP and ATP are usually used at a concentration of 0.01-100 mmol/l.

N-Acetylneuraminic acid or N-acetylmannosamine formed in the aqueous medium can be determined by using a carbohydrate analysis system (Dionex) or the like [Anal. Biochem., 189, 151 (1990)].

N-Acetylneuraminic acid or N-acetylmannosamine can be recovered from the reaction mixture by ordinary methods using active carbon, ion-exchange resins, etc.

Certain embodiments of the present invention are illustrated in the following examples. These examples are not to be construed as limiting the scope of the invention.

EXAMPLE 1

Construction of a Strain Expressing N-Acetylneuraminic Acid Aldolase Gene Derived from *Escherichia coli*

*Escherichia coli* W3110 (ATCC 27325) was cultured by the method described in Current Protocols in Molecular Biology and the chromosomal DNA of the microorganism was isolated and purified.

The DNA primer shown in SEQ ID NO: 3 and the DNA primer shown in SEQ ID NO: 4 were synthesized by using a DNA synthesizer (Model 8905, PerSeptive Biosystems).

PCR was carried out using the above synthetic DNAs as primers and the chromosomal DNA of *Escherichia coli* W3110 (ATCC 27325) as a template. That is, PCR was carried out by 30 cycles, one cycle consisting of reaction at 94° C. for one minute, reaction at 42° C. for 2 minutes and reaction at 72° C. for 3 minutes, using 40 μl of a reaction mixture comprising 0.1 μg of the chromosomal DNA, 0.5 μmol/l each of the primers, 2.5 units of Pfu DNA polymerase (Stratagene), 4 μl of buffer for Pfu DNA polymerase (10×) (Stratagene) and 200 μmol/l each of deoxyNTPs.

One-tenth of the resulting reaction mixture was subjected to agarose gel electrophoresis to confirm that the desired fragment was amplified. Then, the remaining reaction mixture was mixed with an equal amount of phenol/chloroform (1 vol/1 vol) saturated with TE [10 mmol/l Tris-HCl (pH 8.0), 1 mmol/l EDTA], followed by centrifugation. The obtained upper layer was mixed with a two-fold volume of cold ethanol and allowed to stand at −80° C. for 30 minutes. The resulting mixture was centrifuged to obtain a DNA precipitate.

The DNA precipitate was dissolved in 20 μl of TE and 5 μl of the solution was subjected to reaction to cleave the DNA with restriction enzymes HindIII and BamHI. DNA fragments were separated by agarose gel electrophoresis and a 1.2 kb fragment was recovered using Gene Clean II Kit (Bio 101). pUC19 DNA [Gene, 33, 103 (1985)] (0.2 μg) was cleaved with restriction enzymes HindIII and BamHI. DNA fragments were separated by agarose gel electrophoresis and a 2.7 kb fragment was recovered in the same manner.

The 1.2 kb fragment and 2.7 kb fragment obtained above were subjected to ligation reaction using a ligation kit at 16° C. for 16 hours. *Escherichia coli* NM522 capable of producing pyruvic acid was transformed using the ligation mixture according to the known method described above, spread on LB agar medium containing 50 μg/ml ampicillin, and cultured overnight at 30° C.

Figure 1:
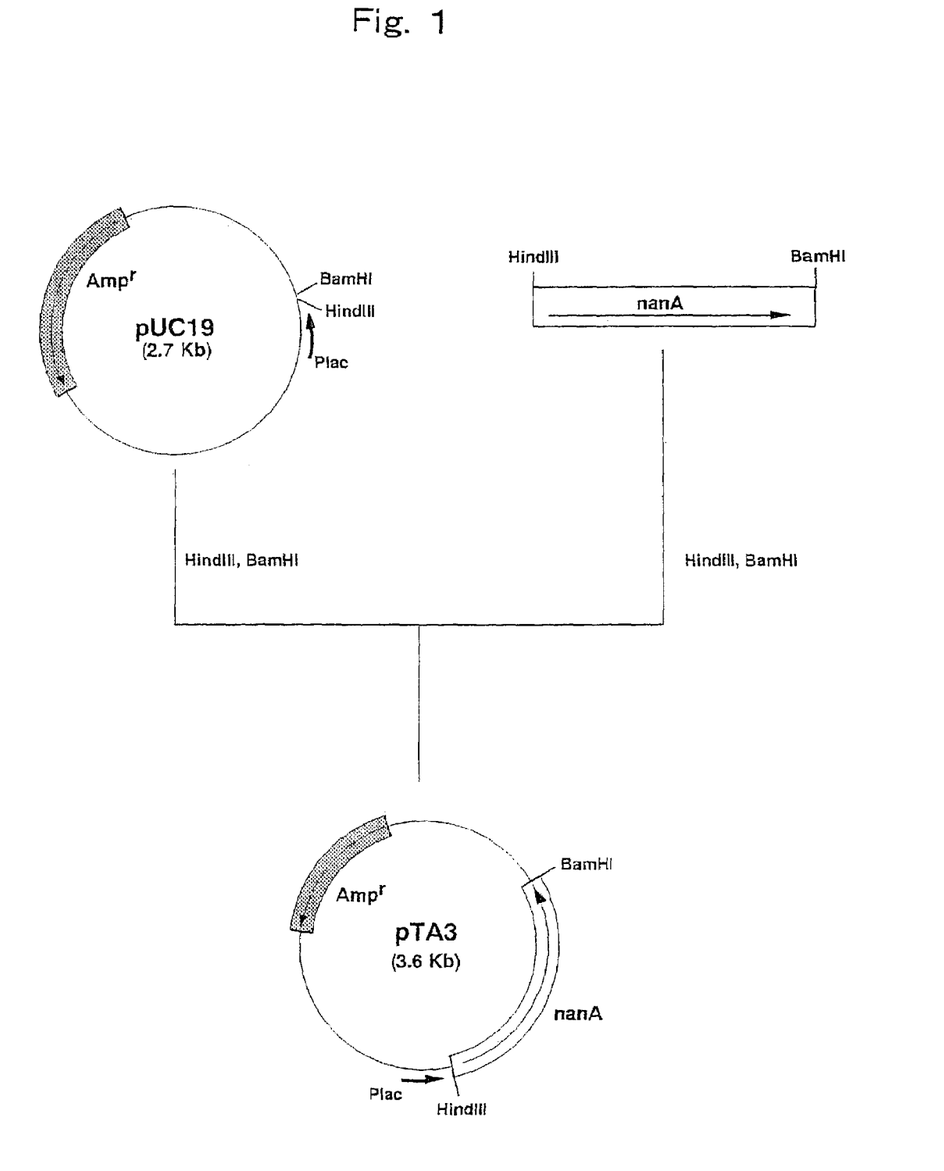
FIG. 1 shows the steps for constructing plasmid pTA3 expressing N-acetylneuraminic acid aldolase.

*Escherichia coli* NM522/pTA3, which is a transformant carrying the N-acetylneuraminic acid aldolase gene, nanA, was obtained from a colony of the transformant that grew on the above medium. A plasmid was extracted from this transformant by a known method to obtain pTA3, which is a plasmid for expression of N-acetylneuraminic acid aldolase gene. The structure of this plasmid was confirmed by digestion with restriction enzymes (FIG. 1).

EXAMPLE 2

Production of N-Acetylneuraminic Acid

*Escherichia coli* NM522/pTA3 obtained in Example 1 was inoculated into 125 ml of LB medium containing 50 μg/ml ampicillin in a 1-l Erlenmeyer flask with baffles, followed by culturing at 28° C. with stirring (220 r.p.m.) for 17 hours. The resulting culture (125 ml) was inoculated into 2.5 l of a liquid medium (pH unadjusted) comprising 10 g/l glucose, 12 g/l Bacto-tryptone (Difco Laboratories Inc.), 24 g/l yeast extract (Difco Laboratories Inc.), 2.3 g/l $KH_2PO_4$, 12.5 g/l $K_2HPO_4$ and 50 μg/ml ampicillin in a 5-l jar fermentor. Culturing was carried out at 37° C. for 6 hours under the conditions of stirring at 600 r.p.m. and aeration at 2.5 l/min. During the culturing, the pH of culture was maintained at 7.0 with 28% aqueous ammonia. Glucose was added, according to need, in the course of culturing. The resulting culture was centrifuged to obtain wet cells. The wet cells could be stored at −20° C. and could be used after thawing, according to need.

A reaction mixture (30 ml) comprising 50 g/l *Escherichia coli* NM522/pTA3 wet cells, 65 g/l fructose, 40 g/l N-acetylmannosamine, 25 g/l $KH_2PO_4$, 5 g/l $MgSO_4.7H_2O$, 5 g/l phytic acid, 4 g/l Nymeen S-215 and 10 ml/l xylene was put into a 200-ml beaker and subjected to reaction at 32° C. for 25 hours with stirring (900 r.p.m.) using a magnetic stirrer. During the reaction, the pH of reaction mixture was maintained at 7.2 with 4 N NaOH, and according to need, fructose and $KH_2PO_4$ were added to the reaction mixture.

After the completion of reaction, the reaction product was analyzed by using a carbohydrate analysis system (DX-500, Dionex) and it was found that 0.34 g/l N-acetylneuraminic acid was formed and accumulated in the reaction mixture.

EXAMPLE 3

Construction of a Strain Expressing N-Acetylneuraminic Acid Synthetase Gene Derived from *Escherichia coli*

*Escherichia coli* K235 (ATCC 13027) was cultured by the method described in Current Protocols in Molecular Biology and the chromosomal DNA of the microorganism was isolated and purified.

The DNA primer shown in SEQ ID NO: 5 and the DNA primer shown in SEQ ID NO: 6 were synthesized by using a DNA synthesizer (Model 8905, PerSeptive Biosystems).

PCR was carried out using the above synthetic DNAs as primers and the chromosomal DNA of *Escherichia coli* K235 (ATCC 13027) as a template. That is, PCR was carried out by 30 cycles, one cycle consisting of reaction at 94° C. for one minute, reaction at 42° C. for 2 minutes and reaction at 72° C. for 3 minutes, using 40 μl of a reaction mixture comprising 0.1 μg of the chromosomal DNA, 0.5 μmol/l each of the primers, 2.5 units of Pfu DNA polymerase (Stratagene), 4 μl of buffer for Pfu DNA polymerase (10×) (Stratagene) and 200 μL mol/l each of deoxyNTPs.

One-tenth of the resulting reaction mixture was subjected to agarose gel electrophoresis to confirm that the desired fragment was amplified. Then, the remaining reaction mixture was mixed with an equal amount of phenol/chloroform (1 vol/1 vol) saturated with TE, followed by centrifugation. The obtained upper layer was mixed with a two-fold volume of cold ethanol and allowed to stand at −80° C. for 30 minutes.

The resulting mixture was centrifuged to obtain a DNA precipitate.

The DNA precipitate was dissolved in 20 µl of TE and 5 µl of the solution was subjected to reaction to cleave the DNA with restriction enzymes ClaI and BamHI. DNA fragments were separated by agarose gel electrophoresis and a 1.1 kb fragment was recovered using Gene Clean II Kit (Bio 101). pPAC31 DNA (WO98/12343) (0.2 µg) was cleaved with restriction enzymes ClaI and BamHI. DNA fragments were separated by agarose gel electrophoresis and a 5.5 kb fragment was recovered in the same manner.

The 1.1 kb fragment and 5.5 kb fragment obtained above were subjected to ligation reaction using a ligation kit at 16° C. for 16 hours. *Escherichia coli* NM522 capable of producing phosphoenolpyruvic acid was transformed using the ligation mixture according to the known method described above, spread on LB agar medium containing 50 µg/ml ampicillin, and cultured overnight at 30° C.

Figure 2:
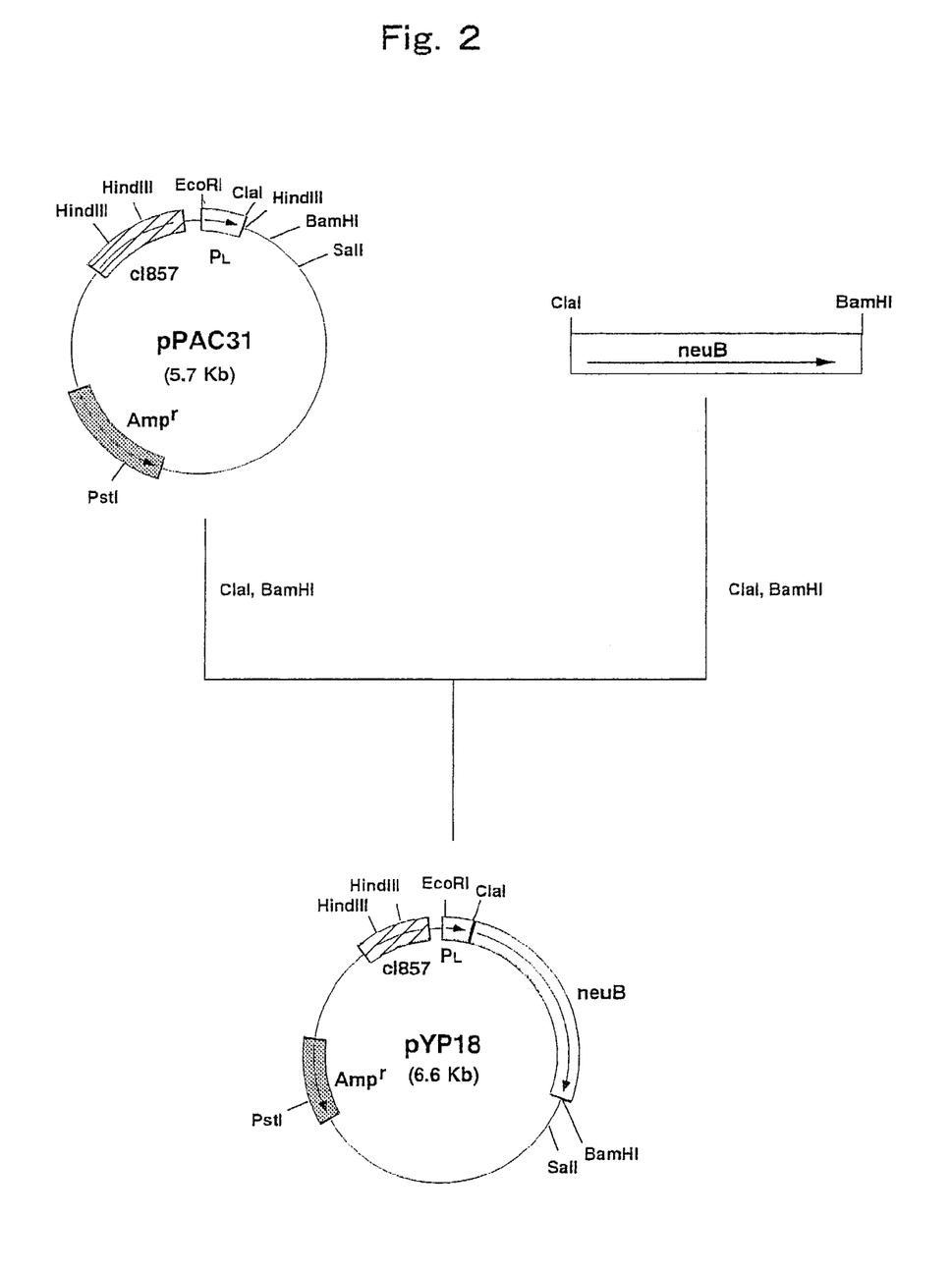
FIG. 2 shows the steps for constructing plasmid pYP18 expressing N-acetylneuraminic acid synthetase.

*Escherichia coli* NM522/pYP18, which is a transformant carrying the N-acetylneuraminic acid synthetase gene, neuB, was obtained from a colony of the transformant that grew on the above medium. A plasmid was extracted from this transformant by a known method to obtain pYP18, which is a plasmid for expression of N-acetylneuraminic acid synthetase gene. The structure of this plasmid was confirmed by digestion with restriction enzymes (FIG. 2).

EXAMPLE 4

Production of N-Acetylneuraminic Acid

*Escherichia coli* NM522/pYP18 obtained in Example 3 was inoculated into 125 ml of LB medium containing 50 µg/mL ampicillin in a 1-1 Erlenmeyer flask with baffles, followed by culturing at 28° C. with stirring (220 r.p.m.) for 17 hours. The resulting culture (125 ml) was inoculated into 2.5 l of a liquid medium (pH unadjusted) comprising 10 g/l glucose, 12 g/l Bacto-tryptone (Difco Laboratories Inc.), 24 g/l yeast extract (Difco Laboratories Inc.), 2.3 g/l $KH_2PO_4$, 12.5 g/l $K_2HPO_4$ and 50 µg/ml ampicillin in a 5-1 jar fermentor. Culturing was carried out at 37° C. for 4 hours and then at 40° C. for 3 hours, under the conditions of stirring at 600 r.p.m. and aeration at 2.5 l/min. During the culturing, the pH of culture was maintained at 7.0 with 28% aqueous ammonia. Glucose was added, according to need, in the course of culturing.

The resulting culture was centrifuged to obtain wet cells. The wet cells could be stored at −20° C. and could be used after thawing, according to need.

A reaction mixture (30 ml) comprising 50 g/l *Escherichia coli* NM522/pYP18 wet cells, 65 g/l fructose, 40 g/l N-acetylmannosamine, 25 g/l $KH_2PO_4$, 5 g/l $MgSO_4.7H_2O$, 5 g/l phytic acid, 4 g/l Nymeen S-215 and 10 ml/l xylene was put into a 200-ml beaker and subjected to reaction at 32° C. for 19 hours with stirring (900 r.p.m.) using a magnetic stirrer. During the reaction, the pH of reaction mixture was maintained at 7.2 with 4 N NaOH, and according to need, fructose and $KH_2PO_4$ were added to the reaction mixture.

After the completion of reaction, the reaction product was analyzed by using a carbohydrate analysis system (DX-500, Dionex) and it was found that 1.4 g/l N-acetylneuraminic acid was formed and accumulated in the reaction mixture.

EXAMPLE 5

Production of N-Acetylneuraminic Acid

*Escherichia coli* NM522/pYP18 obtained in Example 3 was cultured according to the method described in Example 2 and the resulting culture was centrifuged to obtain wet cells. The wet cells could be stored at −20° C. and could be used after thawing, according to need.

*Corynebacterium ammoniagenes* ATCC 21170 was inoculated into 25 ml of a liquid medium comprising 50 µl glucose, 10 g/l polypeptone (Nihon Pharmaceutical Industrial Co., Ltd.), 10 g/l yeast extract (Oriental Yeast Co., Ltd.), 5 g/l urea, 5 g/l $(NH_4)_2SO_4$, 1 g/l $KH_2PO_4$, 3 g/l $K_2HPO_4$, 1 g/l $MgSO_4.7H_2O$, 0.1 g/l $CaCl_2.2H_2O$, 10 mg/l $FeSO_4.7H_2O$, 10 mg/l $ZnSO_4.7H_2O$, 20 mg/l $MnSO_4.4-6H_2O$, 20 mg/l L-cysteine, 10 mg/l calcium D-pantothenate, 5 mg/l vitamin $B_1$, 5 mg/l nicotinic acid and 30µ g/l biotin (adjusted to pH 7.2 with 10 N NaOH) in a 300-ml Erlenmeyer flask with baffles, followed by culturing at 28° C. with stirring (220 r.p.m.) for 24 hours.

The resulting culture (20 ml) was inoculated into 250 ml of a liquid medium having the same composition as above in a 2-1 Erlenmeyer flask with baffles, followed by culturing at 28° C. with stirring (220 r.p.m.) for 24 hours. The obtained culture was used as a seed culture.

The seed culture (250 ml) was inoculated into 2.25 l of a liquid medium comprising 150 g/l glucose, 5 g/l meat extract (Kyokuto Pharmaceutical Ind. Co., Ltd.), 10 g/l $KH_2PO_4$, 10 µl $K_2HPO_4$, 10 g/l $MgSO_4.7H_2O$, 0.1 g/l $CaCl_2.2H_2O$, 20 mg/l $FeSO_4.7H_2O$, 10 mg/l $ZnSO_4.7H_2O$, 20 mg/l $MnSO_4.4-6H_2O$ (separately sterilized), 15 mg/l β-alanine (separately sterilized), 20 mg/i L-cysteine, 100 µg/l biotin, 2 g/l urea and 5 mg/l vitamin $B_1$ (separately sterilized) (adjusted to pH 7.2 with 10 N NaOH) in a 5-1 jar fermentor. Culturing was carried out at 32° C. for 24 hours under the conditions of stirring at 600 r.p.m. and aeration at 2.5 l/min. During the culturing, the pH of culture was maintained at 6.8 with 28% aqueous ammonia.

The resulting culture was centrifuged to obtain wet cells. The wet cells could be stored at −20° C. and could be used after thawing, according to need.

A reaction mixture (30 ml) comprising 50 g/l *Escherichia coli* NM522/pYP18 wet cells, 150 g/l *Corynebacterium ammoniagenes* ATCC 21170 wet cells, 65 g/l fructose, 40 g/l N-acetylmannosamine, 25 g/l $KH_2PO_4$, 5 µl $MgSO_4.7H_2O$, 5 g/l phytic acid, 4 g/l Nymeen S-215 and 10 ml/l xylene was put into a 200-ml beaker and subjected to reaction at 32° C. for 6 hours with stirring (900 r.p.m.) using a magnetic stirrer. During the reaction, the pH of reaction mixture was maintained at 7.2 with 4 N NaOH, and according to need, fructose and $KH_2PO_4$ were added to the reaction mixture.

After the completion of reaction, the reaction product was analyzed by using a carbohydrate analysis system (DX-500, Dionex) and it was found that 3.1 g/l N-acetylneuraminic acid was formed and accumulated in the reaction mixture.

EXAMPLE 6

Construction of a Strain Expressing
N-Acetylglucosamine 2-Epimerase Gene Derived
from *Synechocystis*

Blast Search of Genbank and a similarity search on CyanoBase is a database of the genomic sequence of *Synechocystis* sp. (PCC6803), were conducted with the amino acid sequence of N-acetylglucosamine 2-epimerase derived from pig [J. Biol. Chem., 271, 16294 (1996)] as a query. As a result, the above amino acid sequence showed a high homology to the sequence derived from *Synechocystis* sp. (PCC6803) described as a renin-binding protein (slr1975).

*Synechocystis* sp. (PCC6803) was cultured by the method described in J. Gen. Microbiol., 111, 1 (1979), and the chromosomal DNA of the microorganism was isolated and purified by the method described in Current Protocols in Molecular Biology.

PCR was carried out according to the method described in Example 1 using the DNAs shown in SEQ ID NOS: 7 and 8 which had been synthesized by using a DNA synthesizer (Model 8905, PerSeptive Biosystems) as primers and the chromosomal DNA of *Synechocystis* sp. (PCC6803) as a template.

One-tenth of the resulting reaction mixture was subjected to agarose gel electrophoresis to confirm that the desired fragment was amplified. Then, the remaining reaction mixture was mixed with an equal amount of phenol/chloroform (1 vol/1 vol) saturated with TE.

The resulting mixture was centrifuged and the obtained upper layer was mixed with a two-fold volume of cold ethanol and allowed to stand at −80° C. for 30 minutes. The resulting mixture was centrifuged to obtain a DNA precipitate.

The DNA precipitate was dissolved in 20 μl of TE and 5 μl of the solution was subjected to reaction to cleave the DNA with restriction enzymes ClaI and BamHI. DNA fragments were separated by agarose gel electrophoresis and a 1.2 kb fragment was recovered using Gene Clean II Kit (Bio 101).

pPAC31 DNA (0.2 μg) was cleaved with restriction enzymes ClaI and BamHI. DNA fragments were separated by agarose gel electrophoresis and a 5.5 kb fragment was recovered in the same manner.

The 1.2 kb fragment and 5.5 kb fragment obtained above were subjected to ligation reaction using a ligation kit at 16° C. for 16 hours.

*Escherichia coli* NM522 was transformed using the ligation mixture according to the known method described above, spread on LB agar medium containing 50 μg/ml ampicillin, and cultured overnight at 30° C.

Figure 3:
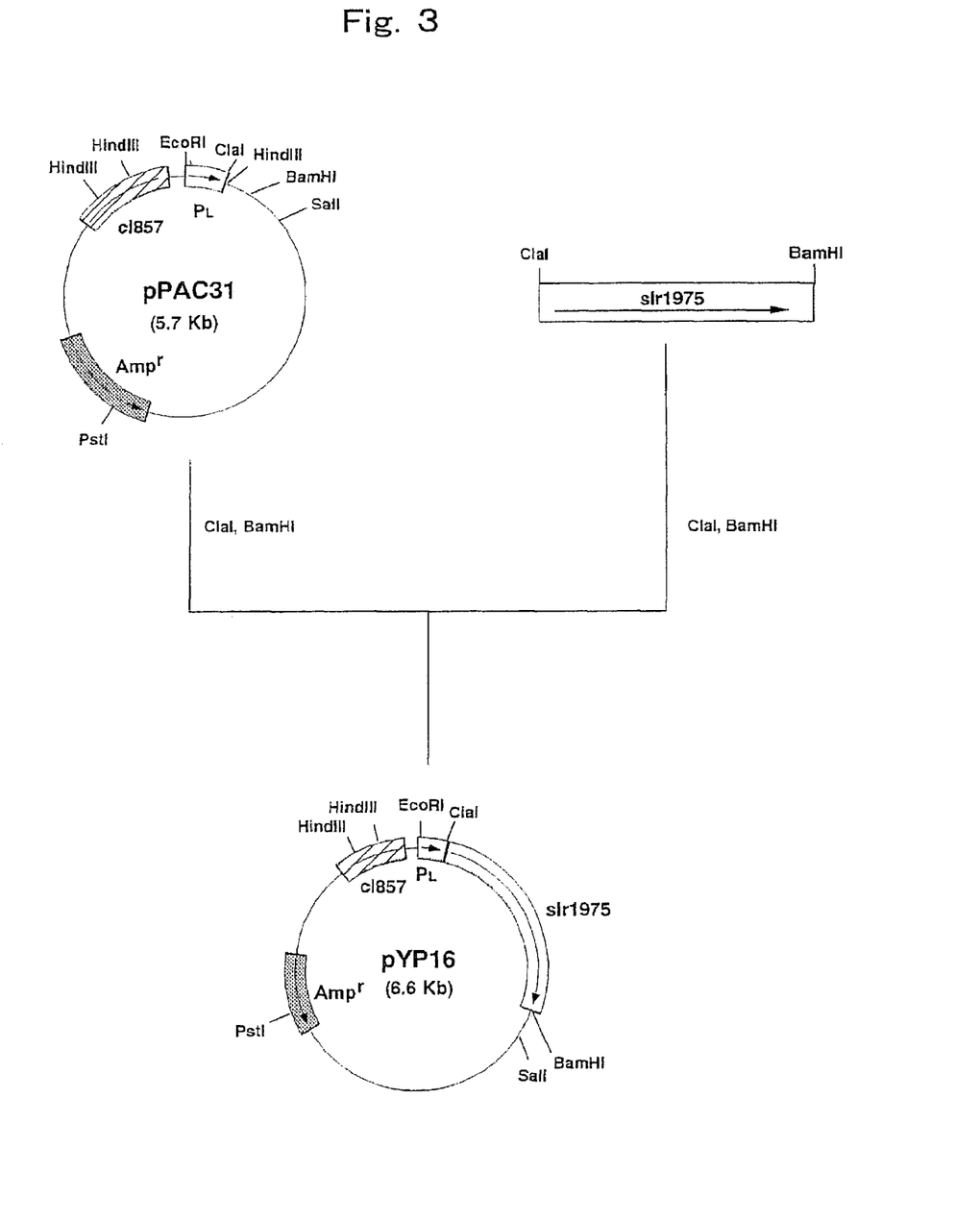
FIG. 3 shows the steps for constructing plasmid pYP16 expressing N-acetylglucosamine 2-epimerase.

*Escherichia coli* NM522/pYP16, which is a transformant carrying the DNA encoding N-acetylglucosamine 2-epimerase derived from *Synechocystis* sp., was obtained from a colony of the transformant that grew on the above medium. A plasmid was extracted from this transformant by a known method to obtain expression plasmid pYP16. The structure of this plasmid was confirmed by digestion with restriction enzymes (FIG. 3).

EXAMPLE 7

Production of N-Acetylneuraminic Acid

*Escherichia coli* NM522/pTA3 obtained in Example 1 was cultured according to the method described in Example 2 and the resulting culture was centrifuged to obtain wet cells. The wet cells could be stored at −20° C. and could be used after thawing, according to need.

*Escherichia coli* NM522/pYP16 obtained in Example 6 was inoculated into 125 ml of LB medium containing 50 μg/ml ampicillin in a 1-1 Erlenmeyer flask with baffles, followed by culturing at 28° C. with stirring (220 r.p.m.) for 17 hours. The resulting culture (125 ml) was inoculated into 2.5 l of a liquid medium (pH unadjusted) comprising 10 g/l glucose, 12 g/l Bacto-tryptone (Difco Laboratories Inc.), 24 g/l yeast extract (Difco Laboratories Inc.), 2.3 g/l $KH_2PO_4$, 12.5 g/l $K_2HPO_4$ and 50 μg/ml ampicillin in a 5-l jar fermentor. Culturing was carried out at 30° C. for 4 hours and then at 40° C. for 3 hours, under the conditions of stirring at 600 r.p.m. and aeration at 2.5 l/min. During the culturing, the pH of culture was maintained at 7.0 with 28% aqueous ammonia. Glucose was added, according to need, in the course of culturing.

The resulting culture was centrifuged to obtain wet cells. The wet cells could be stored at −20° C. and could be used after thawing, according to need.

*Corynebacterium ammoniagenes* ATCC 21170 was cultured according to the method described in Example 5 and the resulting culture was centrifuged to obtain wet cells. The wet cells could be stored at −20° C. and could be used after thawing, according to need.

A reaction mixture (30 ml) comprising 50 g/l *Escherichia coli* NM522/pTA3 wet cells, 50 g/l *Escherichia coli* NM522/pYP16 wet cells, 150 g/l *Corynebacterium ammoniagenes* ATCC 21170 wet cells, 65 g/l fructose, 180 g/l N-acetylglucosamine, 25 g/l $KH_2PO_4$, 5 g/l $MgSO_4.7H_2O$, 5 g/l phytic acid, 4 g/l Nymeen S-215 and 10 ml/l xylene was put into a 200-ml beaker and subjected to reaction at 32° C. for 24 hours with stirring (900 r.p.m.) using a magnetic stirrer. During the reaction, the pH of reaction mixture was maintained at 7.2 with 4 N NaOH, and according to need, fructose and $KH_2PO_4$ were added to the reaction mixture.

After the completion of reaction, the reaction product was analyzed by using a carbohydrate analysis system (DX-500, Dionex) and it was found that 1.0 g/l N-acetylneuraminic acid was formed and accumulated in the reaction mixture.

EXAMPLE 8

Production of N-Acetylneuraminic Acid

*Escherichia coli* NM522/pYP18 obtained in Example 3 and *Escherichia coli* NM522/pYP16 obtained in Example 6 were cultured according to the methods described in Examples 4 and 7, respectively, and the resulting cultures were centrifuged to obtain wet cells. The wet cells could be stored at −20° C. and could be used after thawing, according to need.

A reaction mixture (30 ml) comprising 50 g/l *Escherichia coli* NM522/pYP16 wet cells, 50 g/l *Escherichia coli* NM522/pYP18 wet cells, 65 g/l fructose, 180 g/l N-acetylglucosamine, 25 g/l $KH_2PO_4$, 5 g/l $MgSO_4.7H_2O$, 5 g/l phytic acid, 4 g/l Nymeen S-215 and 10 ml/l xylene was put into a 200-ml beaker and subjected to reaction at 32° C. for 11 hours with stirring (900 r.p.m.) using a magnetic stirrer. During the reaction, the pH of reaction mixture was maintained at 7.2 with 4 N NaOH, and according to need, fructose and $KH_2PO_4$ were added to the reaction mixture.

After the completion of reaction, the reaction product was analyzed by using a carbohydrate analysis system (DX-500, Dionex) and it was found that 1.3 g/l N-acetylneuraminic acid was formed and accumulated in the reaction mixture.

EXAMPLE 9

Production of N-Acetylneuraminic Acid

*Escherichia coli* NM522/pYP18 obtained in Example 3 and *Escherichia coli* NM522/pYP16 obtained in Example 6 were cultured according to the methods described in Examples 4 and 7, respectively, and the resulting cultures were centrifuged to obtain wet cells. The wet cells could be stored at −20° C. and could be used after thawing, according to need.

Corynebacterium ammoniagenes ATCC 21170 was cultured according to the method described in Example 5 and the resulting culture was centrifuged to obtain wet cells. The wet cells could be stored at −20° C. and could be used after thawing, according to need.

A reaction mixture (30 ml) comprising 50 g/l Escherichia coli NM522/pYP16 wet cells, 50 g/l Escherichia coli NM522/pYP18 wet cells, 150 g/l Corynebacterium ammoniagenes ATCC 21170 wet cells, 65 g/l fructose, 180 g/l N-acetylglucosamine, 25 g/l $KH_2PO_4$, 5 g/l $MgSO_4 \cdot 7H_2O$, 5 g/l phytic acid, 4 g/l Nymeen S-215 and 10 ml/l xylene was put into a 200-ml beaker and subjected to reaction at 32° C. for 24 hours with stirring (900 r.p.m.) using a magnetic stirrer. During the reaction, the pH of reaction mixture was maintained at 7.2 with 4 N NaOH, and according to need, fructose and $KH_2PO_4$ were added to the reaction mixture.

After the completion of reaction, the reaction product was analyzed by using a carbohydrate analysis system (DX-500, Dionex) and it was found that 4.3 g/l N-acetylneuraminic acid was formed and accumulated in the reaction mixture.

EXAMPLE 10

Production of N-Acetylneuraminic Acid

Escherichia coli NM522/pYP18 obtained in Example 3 and Escherichia coli NM522/pYP16 obtained in Example 6 were cultured according to the methods described in Examples 4 and 7, respectively, and the resulting cultures were centrifuged to obtain wet cells. The wet cells could be stored at −20° C. and could be used after thawing, according to need.

Corynebacterium ammoniagenes ATCC 21170 was cultured according to the method described in Example 5 and the resulting culture was centrifuged to obtain wet cells. The wet cells could be stored at −20° C. and could be used after thawing, according to need.

A reaction mixture (30 ml) comprising 50 g/l Escherichia coli NM522/pYP16 wet cells, 50 g/l Escherichia coli NM522/pYP18 wet cells, 150 g/l Corynebacterium ammoniagenes ATCC 21170 wet cells, 100 g/l glucose, 180 g/l N-acetylglucosamine, 5 g/l adenine, 15 g/l $KH_2PO_4$, 5 g/l $MgSO_4 \cdot 7H_2O$, 5 g/l phytic acid, 4 g/l Nymeen S-215 and 10 ml/l xylene was put into a 200-ml beaker and subjected to reaction at 32° C. for 22 hours with stirring (900 r.p.m.) using a magnetic stirrer. During the reaction, the pH of reaction mixture was maintained at 7.2 with 4 N NaOH, and according to need, glucose and $KH_2PO_4$ were added to the reaction mixture.

After the completion of reaction, the reaction product was analyzed by using a carbohydrate analysis system (DX-500, Dionex) and it was found that 12.3 g/l N-acetylneuraminic acid was formed and accumulated in the reaction mixture.

What is claimed is:

1. A process for producing N-acetylneuraminic acid which comprises:

allowing (i) a culture or treated culture of a microorganism having N-acetylneuraminic acid synthetase activity, (ii) a culture or treated culture of a microorganism belonging to the genus *Escherichia* or *Corynebacterium* and capable of producing phosphoenolpyruvic acid, (iii) N-acetylmannosamine, and (iv) glucose or fructose to be present in an aqueous medium to form and accumulate N-acetylneuraminic acid in aqueous medium, wherein said N-acetylmannosamine is produced in said aqueous medium or added thereto, and said glucose or fructose is added to said aqueous medium, and wherein free phosphoenolpyruvic acid is not added to said aqueous medium; and recovering N-acetylneuraminic acid from the aqueous medium, wherein said treated cultures are independently selected from the group consisting of concentrated culture, dried culture, cells obtained by centrifuging the culture, dried cells, freeze-dried cells, immobilized cells, enzyme-treated cells, surfactant-treated cells and solvent-treated cells, wherein said treated culture continues to have the same enzyme activity as the culture.

2. The process according to claim 1, wherein said N-acetylmannosamine is produced by allowing (a) a culture or treated culture of a microorganism having N-acetylglucosamine 2-epimerase activity, and (b) N-acetylglucosamine to be present in an aqueous medium to form and accumulate N-acetylmannosamine in the aqueous medium, wherein said treated culture is selected from the group consisting of concentrated culture, dried culture, cells obtained by centrifuging the culture, dried cells, freeze-dried cells, immobilized cells, enzyme-treated cells, surfactant-treated cells and solvent-treated cells, wherein said treated culture continues to have the same N-acetylglucosamine 2-epimerase activity as the culture.

3. The process according to claim 2, wherein said microorganism having N-acetylglucosamine 2-epimerase activity carries a recombinant DNA comprising DNA encoding N-acetylglucosamine 2-epimerase and a vector.

4. The process according to any of claims 1-3, wherein said microorganism having N-acetylneuraminic acid synthetase activity belongs to a genus selected from the group consisting of *Escherichia, Neisseria* and *Streptococcus.*

5. The process according to claim 4, wherein said microorganism capable of producing phosphoenolpyruvic acid is *Escherichia.*

6. The process according to claim 4, wherein said microorganism having N-acetylneuraminic acid synthetase activity is *Escherichia coli.*

7. The process according to claim 5, wherein said microorganism having N-acetylneuraminic acid synthetase activity is *Escherichia coli.*

8. The process according to claim 5, wherein said microorganism capable of producing phosphoenolpyruvic acid is *Escherichia coli.*

9. The process according to claim 4, wherein said microorganism capable of producing phosphoenolpyruvic acid is *Corynebacterium ammoniagenes, Corynebacterium glutamicum* or *Corynebacterium acetoacidophilum.*

10. The process according to claim 5, wherein said microorganism capable of producing phosphoenolpyruvic acid is *Corynebacterium ammoniagenes, Corynebacterium glutamicum* or *Corynebacterium acetoacidophilum.*

* * * * *